(12) United States Patent
Turner-Fernback

(10) Patent No.: US 11,688,380 B2
(45) Date of Patent: Jun. 27, 2023

(54) EAR DEVICE WITH DYNAMIC NOISE ATTENUATION AND GENERATION

(71) Applicant: Deborah Caroline Turner-Fernback, Berlin (DE)

(72) Inventor: Deborah Caroline Turner-Fernback, Berlin (DE)

(*) Notice: Subject to any disclaimer, the term of this patent is extended or adjusted under 35 U.S.C. 154(b) by 61 days.

(21) Appl. No.: 17/277,981

(22) PCT Filed: Sep. 20, 2019

(86) PCT No.: PCT/GB2019/052654
§ 371 (c)(1),
(2) Date: Mar. 19, 2021

(87) PCT Pub. No.: WO2020/058730
PCT Pub. Date: Mar. 26, 2020

(65) Prior Publication Data
US 2021/0375253 A1    Dec. 2, 2021

(30) Foreign Application Priority Data

Sep. 20, 2018 (GB) .................................. 1815368

(51) Int. Cl.
*G10K 11/175* (2006.01)
*G10K 11/178* (2006.01)
(Continued)

(52) U.S. Cl.
CPC .......... *G10K 11/1752* (2020.05); *A61F 9/045* (2013.01); *A61F 11/14* (2013.01); *G10K 11/1785* (2018.01); *A61F 11/145* (2022.01)

(58) Field of Classification Search
CPC .......... G10K 11/1752; G10K 11/1785; G10K 11/178; G10K 2210/00; G10K 2210/3027;
(Continued)

(56) References Cited

U.S. PATENT DOCUMENTS

| 3,805,782 A | 4/1974 | Welch |
| 4,833,719 A | 5/1989 | Carme |

(Continued)

FOREIGN PATENT DOCUMENTS

| CN | 2400079 Y | 10/2000 |
| CN | 201154137 Y | 11/2008 |

(Continued)

OTHER PUBLICATIONS

Hibernate—Introducing the world's first sound-reducing sleep mask, 7 Pages.

(Continued)

*Primary Examiner* — David L Ton
(74) *Attorney, Agent, or Firm* — Deborah Turner-Fernback

(57) ABSTRACT

An ear-and-eye mask (10) is provided comprising a noise-attenuation-and-generation assembly (46) having a digital domain, the noise-attenuation-and-generation assembly comprising, in the digital domain, a noise cancelling-circuit (48) and a noise masking circuit (64), wherein the noise-cancelling circuit (48) receives an input from an audio capture device (56) thereof which communicates with the noise masking circuit (64). An adaptive spectral noise analyser and generator is provided which determines an unwanted remnant signal comprising the leftover unwanted frequency and/or volume after noise cancellation, and wherein the noise attenuation-and-generation assembly (46) then determines and generates a compensation frequency and/or volume for countering this unwanted remnant signal following noise attenuation for output by a speaker (36) through a stem (40) direct to the user's ears.

15 Claims, 6 Drawing Sheets

(51) Int. Cl.
*A61F 9/04* (2006.01)
*A61F 11/14* (2006.01)

(58) Field of Classification Search
CPC ............. G10K 2210/3026; A61F 11/14; A61F 11/145; A61F 9/045
See application file for complete search history.

(56) References Cited

U.S. PATENT DOCUMENTS

| | | |
|---|---|---|
| 6,735,316 B1 | 5/2004 | Wurtz |
| 7,065,219 B1 | 6/2006 | Abe |
| 7,202,774 B2 | 4/2007 | Hoyle |
| 7,466,838 B1 | 12/2008 | Moseley |
| 8,306,237 B2 | 11/2012 | Connor |
| 2005/0046549 A1 | 3/2005 | Hoyle |
| 2007/0160251 A1 | 7/2007 | Gabriel |
| 2008/0250547 A1 | 10/2008 | Frank |
| 2011/0209273 A1 | 9/2011 | Fountain |
| 2011/0235813 A1 | 9/2011 | Gauger |
| 2013/0255697 A1 | 10/2013 | Thompson |
| 2014/0303428 A1 | 10/2014 | Berka |
| 2015/0281829 A1 | 10/2015 | Gauger, Jr. |
| 2016/0346129 A1 | 12/2016 | Schaefer |
| 2017/0064060 A1 | 3/2017 | Agrawal |
| 2017/0230744 A1 | 8/2017 | Schrader |
| 2017/0252533 A1 | 9/2017 | Genereux |
| 2017/0264994 A1 | 9/2017 | Gordon |
| 2017/0323630 A1 | 11/2017 | Stickney |
| 2017/0352342 A1 | 12/2017 | Lee |
| 2018/0357995 A1 | 12/2018 | Lee |

FOREIGN PATENT DOCUMENTS

| | | |
|---|---|---|
| CN | 202800200 U | 3/2013 |
| CN | 103445327 A | 12/2013 |
| CN | 203446002 U | 2/2014 |
| CN | 107224349 A | 10/2017 |
| EP | 0935236 A1 | 8/1999 |
| EP | 1438709 A1 | 7/2004 |
| GB | 2188210 A | 9/1987 |
| GB | 2265790 A | 10/1993 |
| GB | 2561858 A | 10/2018 |
| JP | 2000005223 A | 1/2000 |
| JP | 2006223608 A | 8/2006 |
| JP | 2007267310 A | 10/2007 |
| JP | 2012165829 A | 9/2012 |
| KR | 20020093678 A | 12/2002 |
| KR | 20030037253 A | 5/2003 |
| KR | 20120021614 A | 3/2012 |
| KR | 20130005802 A | 1/2013 |
| KR | 20140039452 A | 4/2014 |
| KR | 20160093278 A | 8/2016 |
| WO | 2011137463 A2 | 11/2011 |
| WO | 2013109597 A2 | 7/2013 |
| WO | 2014171795 A1 | 10/2014 |
| WO | 2017122091 A1 | 7/2017 |
| WO | 2017/196453 A1 | 11/2017 |

OTHER PUBLICATIONS

Amazon—Eye Mask Sleep Headphone with Adjustable Headband wfth Velcro and Integrated Detachable Headphonessoft Slow Rebound Shadow Sleeping Gogglesperfect for Air Travel, 2 Pages.
Amazon—CestMall Eye Mask I Sleep Masks Soft Velvet Wireless Bluetooth 4.1 Sleeping Eye Patch Cover, Adjustable Travel Blinker, Hands-free Phone Call Answer, 2 Pages.
Thoughts to Paper, Comprehensive Patent Search Report, 13 Pages.
International Preliminary report on Patentability in relation to international application No. PCT/GB2019/052654, dated Mar. 23, 2021, 13 pages.
Combined Search and Examination Report under Sections 17 & 18(3) in relation to GB application No. GB1815368.4, dated Feb. 22, 2019, 7 pages.
Response made to Report under Section 18(3) in relation to GB application No. GB1815368.4, dated Oct. 30, 2019, 1 page.
Examination Report under Section 18(3) in relation to GB application No. GB1815368.4, dated May 7, 2020, 1 page.
Examination Report under Section 18(3) in relation to GB application No. GB1815368.4, dated Jul. 24, 2020, 2 pages.
Intention to Grant under Section 18(4) in relation to GB application No. GB1815368.4, dated Nov. 5, 2020, 2 pages.
Intention to Grant under Section 18(4) in relation to GB application No. GB2019234.0, dated Nov. 12, 2021, 2 pages.
Combined Search and Examination Report under Sections 17 and 18(3) in relation to GB application No. GB2019234.0, dated Mar. 25, 2021, 6 pages.

EAR DEVICE WITH DYNAMIC NOISE ATTENUATION AND GENERATION

The present invention relates to an ear device for creating enhanced napping conditions or periods of quiet, preferably but not necessarily exclusively for use in creating suitable napping conditions for a user, which may be used in combination with a control application on an external device. The invention also relates to a method of creating enhanced quiet for a user.

Studies have proven that daytime napping has medical benefits for individuals, in particular for heart health, brain function, and efficient digestion, which is essential for a strong immune system. Napping also improves skin condition and helps to combat obesity by reducing ghrelin levels in the stomach, the hormones which stimulate appetite. Without a nap, Magnetic Resonance Imaging (MRI) scans have shown that brain activity declines as the day progresses.

Noise is also a cause for increased stress levels by activation of the amygdala, an almond shaped structure in the brain, causing release of the stress hormone cortisol, with its resultant health implications.

However, particularly in urban environments, there is significant noise pollution, which is detrimental to napping, and it is anticipated that by 2050, 66% of the world's population will be living in cities. Environmental noise, from things like road traffic, trains, planes and wind turbines, is a significant policy issue for the World Health Organization. Research in Europe suggests that noise disturbance can cause real health side effects, and the WHO estimates Western Europeans lose 1 million years of healthy life due to traffic-related noise. Even if the individual does not nap, the allotted periods of quiet will therefore be conducive to improved health.

Napping is best undertaken in accordance with an individual's circadian rhythm, that is, the body's natural 24 hour cycle. For the majority of individuals, this means that the nap is best taken in the late morning or early afternoon, typically for a period of between 10 and 90 minutes. Shift workers, however, may have different cycles, and may nap at later times.

It has been shown that a 10 to 20 minute nap can be sufficient to clear out short-term memories, freeing up the brain for other activities, whilst a 20 to 40 minute nap allows the individual to move through the first two stages of a sleep cycle.

This will slow the heart rate, enhance both alertness and concentration, and elevate the individual's mood. Between 40 and 60 minutes, an individual will move into the latter two stages of the sleep cycle when the brain waves slow down significantly and restorative sleep takes place, which allows the brain to make completely new connections, and in addition to the above benefits, significantly increases creative and problem solving skills. Between 60 and 90 minutes, the user completes a full sleep cycle, moving into REM sleep, when brain activity is heightened again and dreams occur. The cycle then repeats. Some researchers have challenged the benefits and importance of REM sleep with mixed views. Most say that REM sleep is essential for making and retaining memories and emotion regulation, whilst others state that REM sleep is when nightmares and traumatic recurring dreams occur, and that the absence thereof is proven to reduce clinical depression.

After an individual has passed from the theta waves of the first two stages of sleep to the slower and higher amplitude delta waves of the third and fourth stages of sleep, the brain is more proficient at blocking external distractions. However, for shorter naps, covering the first two sleep stages, there is a greater risk of external factors waking the individual, which can make napping difficult.

To improve the individual's capacity to nap, blocking out both visual and audible stimuli is preferable. In darkness, the body releases melatonin, the hormone that prepares the body to sleep, and in silence, our sensory guard switches off and the default mode network of the brain is accessed, improving the ability to process and file thoughts and to think deeply and creatively.

There are no ear devices available, which through a combination of attenuation, spectral analysis of the residual signal still audible to the user, and concurrent signal generation based on this analysis, dynamically attenuate noise across the frequency spectrum in real time according to the user's environment as successfully in order to create the necessary quiet required for successful napping or rest. Other ear devices, play chosen media as a distraction from external disturbances, or clean a signal to improve its acoustic delivery and give the impression that the listener is hearing it in a quiet environment, but none are able to offer the user real time intelligent masking which through concurrent signal generation dynamically attenuates at an appropriate frequency content across the frequency spectrum according to the user's environment.

An improved sleep product would be of immediate use in societies which already divide their sleep into two chunks of 6 hours and 1.5 hours, due to the dip experienced around 2 μm, and for societies which already have an established culture of napping, for example in Asia and Southern Europe, albeit many cultures are now discussing and highlighting the importance of the practise and many large companies in the West provide appropriate spaces for their employees to take a nap.

The present invention seeks to provide a portable ear device which is able to obviate the above-referenced problems and provide an enhanced napping experience.

According to a first aspect of the invention, there is provided an ear device for providing quiet for a user, the ear device comprising: a speaker positioned in an enclosure; an audio capture device for capturing the signal the ear would hear; a noise-attenuation-and-generation assembly, which receives a signal from the audio capture device via an amplifier and which comprises, in the electronic domain, a noise cancelling controller and a noise masking circuit which comprises an adaptive spectral noise analyser and generator; the noise-cancelling controller takes the input from the audio capture device and generates a signal which when fed to the speaker substantially cancels the signal in the acoustic domain; the noise masking circuit simultaneously takes the input from the audio capture device, and having determined the residual signal post cancellation by the noise cancelling controller, the adaptive spectral noise analyser and generator dynamically analyse the frequency content of this residual signal and generate a suitable frequency content to dynamically acoustically mask it, which is also sent to the speaker with the signal from the noise cancelling controller.

The provision of this noise-attenuation and generation assembly which is capable of counteracting residual attenuated noise still audible to a user's ear behind passive and/or active noise-dampening members in real time advantageously improves the possibility to provide net quiet to the user, because the residual signal has been both passively and actively attenuated the noise generator of the noise masking circuit can fully dynamically attenuate this left over residual signal dynamically without the generated masking signal being too intrusive. Existing devices do not provide such effective dynamic broad frequency attenuation.

Optionally, the adaptive spectral analyser and generator of the noise masking circuit utilize an algorithm to determine the frequency content of the residual signal, and generate a suitable signal, to mask this residual signal.

The noise masking circuit is consequently dynamically generating a signal with a frequency spectrum corresponding to the content of the residual noise after passive attenuation by the ear device and active cancellation by the noise cancelling controller.

In order to generate the most appropriate digitally manufactured signal to mask any residual sounds still audible to the user after passive and active cancellation, it is preferred that the relevant residual audible sounds be utilised in order to calculate which is the most suitable signal to generate. This may be achieved by the algorithms of the adaptive spectral analyser and generator which analyse the frequency content and then generate the suitable signal, to mask the residual signal.

Optionally, the audio capture device is isolated from the speaker and the signal generated by the noise cancelling controller, must be estimated and applied to the noise masking circuit, whose adaptive spectral noise analyser and generator dynamically analyses the frequency content of this estimated residual signal and generates a compensation frequency content able to acoustically mask this residual signal which is then added to the inverted phase and passed to the loudspeaker.

Optionally, there is no isolation between the audio capture device and the speaker, the acoustic signal from the speaker being constantly fed back to the noise attenuation and generation assembly, by the audio capture device to self adjust.

Optionally, the noise-attenuation-and-generation assembly comprises an adaptive noise cancelling controller and a noise masking circuit and two audio capture devices; one acoustically isolated from the speaker and forming a feedforward noise cancelling path, the second in the same cavity as the speaker and feeding the residual signal back to the noise attenuation and generation assembly to allow for ongoing adjustment.

Either way the device calculates the residual frequency content of any signal still audible to the user post-cancellation and dynamically generates a signal to mask said residual signal offering improved dynamic attenuation across the entire frequency range.

Optionally, the ear device may include an ear covering comprising an outer cup which in use defines a cavity, the outer cup comprising a first passive noise-excluding member, and further passive noise-excluding and absorbing members associated with the outer cup at least a rim of the outer cup.

Optionally, the ear device may be formed as part of an ear-and-eye mask comprising: a mask body having an opaque eye mask positioned to in-use cover a user's eyes and a pair of said ear coverings positioned to in-use cover a user's ears.

Optionally, the ear device may further comprise an audio isolator comprising: either a support stem having a protruding tip which is receivable within a user's aural cavity or the entrance thereof with the loudspeaker positioned at the base of this stem or somewhere along it, the support stem being hollow so as to couple the acoustic output of the loudspeaker into the user's ear comprising a planar biasing element for adjusting a position of the isolator and/or improving an alignment of the speaker; or functions as a cup within a cup, where the audio capture device is being placed in the outer cup of the ear covering.

Optionally, any or all of the noise-cancelling controller, adaptive spectral noise analyser and generator are implemented by an analogue electronic circuit or a digital signal processor or a combination of the two.

Optionally, the noise-attenuation-and generation assembly comprises a personalisation module, the personalisation module being adapted to receive a user input to modify the signal from the noise attenuation and generation assembly; also it may be possible to receive a one-off user input at set up to modify the signal from the noise attenuation and generation assembly according to the user's hearing; or to allow the user to select from a masking signal which contains enough components to substantially cover the full audio frequency range and therefore be able to dynamically mask any residual signal and provide them with a familiar sound; to choose from a frequency setting best suited to the environment they choose to nap in.

Optionally, since users have different hearing capabilities, often having different sensitivities to different parts of the audible spectrum, the output of the speaker may be modified according to a user's personal requirements and environment, whereby after analysis of the residual signal by the spectral analyser and generator, certain frequencies may be boosted or cut according to the tonal components of the residual signal still audible to the user and the dynamically generated masking level in the required frequency band is adjusted, to provide the user with a suitable masking level.

Optionally there may be a timer associated with the noise attenuation and generation assembly, the timer being configured to deactivate the signal from the noise attenuation and generation assembly after a predetermined or user-settable duration and place it into low power mode when the user has finished.

Optionally the ear device may be provided in combination with an external computing device, which allows the noise attenuation and generation assembly to be split between an external computing device and the ear device and communicate with it Optionally there may be a user interface on the ear device or external computer device to permit user control of the noise-attenuation and generation assembly, such as directly affect the personalisation circuit and settings and allow the user to alter settings on other external devices such as nap scheduling, nap tracking, a napping community or interaction with the user's other apps.

Optionally, the ear device may further comprise an onboard power supply which is configured to power at least the noise-attenuation assembly.

According to a second aspect of the invention there is provided an ear device in accordance with the first aspect of the invention which forms part of an ear-and-eye mask, comprising a mask body having an opaque eye mask positioned to in-use cover a user's eyes and a pair of ear devices which may optionally be positioned to in-use cover a user's ears; each ear device comprising an ear covering including an outer cup, which in-use defines a cavity, the outer cup comprising a first passive noise-excluding member, and further passive noise-excluding and absorbing members associated with the outer cup, at at least a rim of the outer cup.

According to a third aspect of the invention, there is provided a method of creating enhanced napping conditions for a user, the method comprising the steps of: a] providing an ear device in accordance with the second aspect of the invention; and b] when a napping or quiet condition is desired, the user wearing the ear device and or ear and eye mask so that the passive and active noise attenuation and digitally dynamically manufactured signal generated to mask any unwanted residual sound after attenuation minimising the effect of external disturbances.

The invention will now be more particularly described, by way of example only, with reference to the accompanying drawings, in which.

Figure 5:
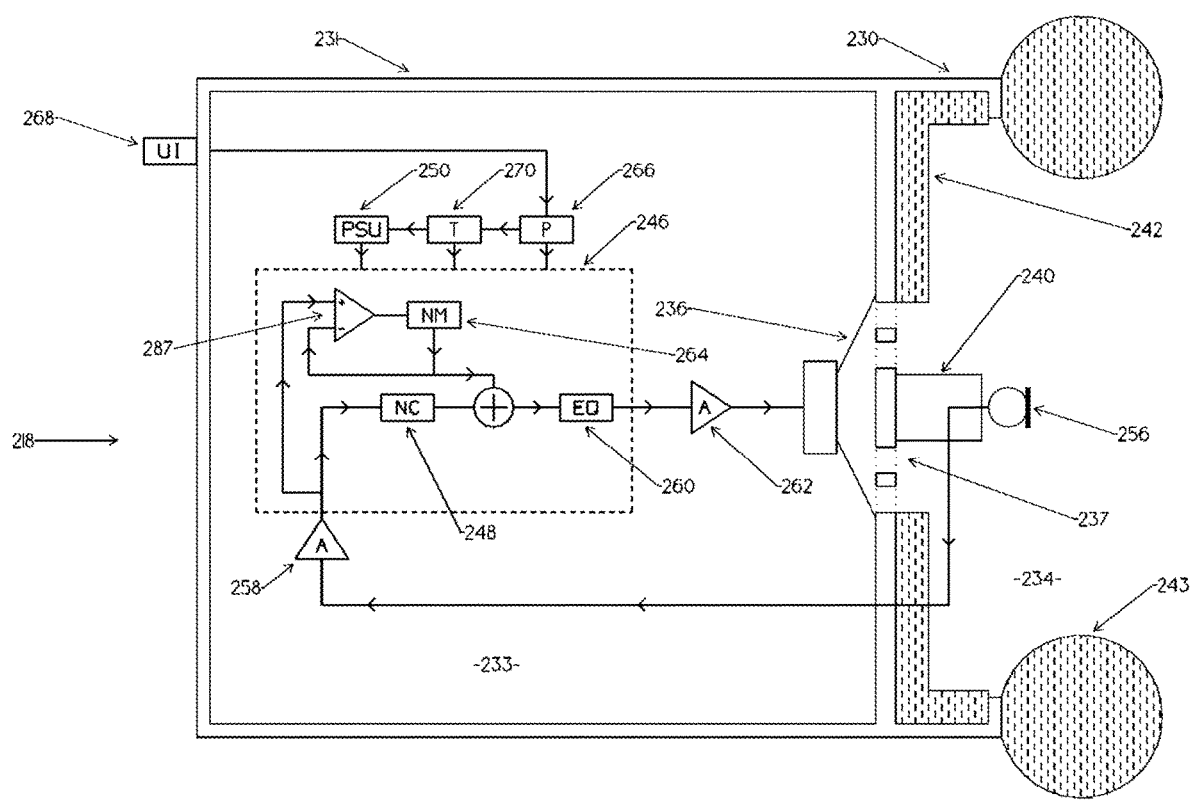
Figure 6:
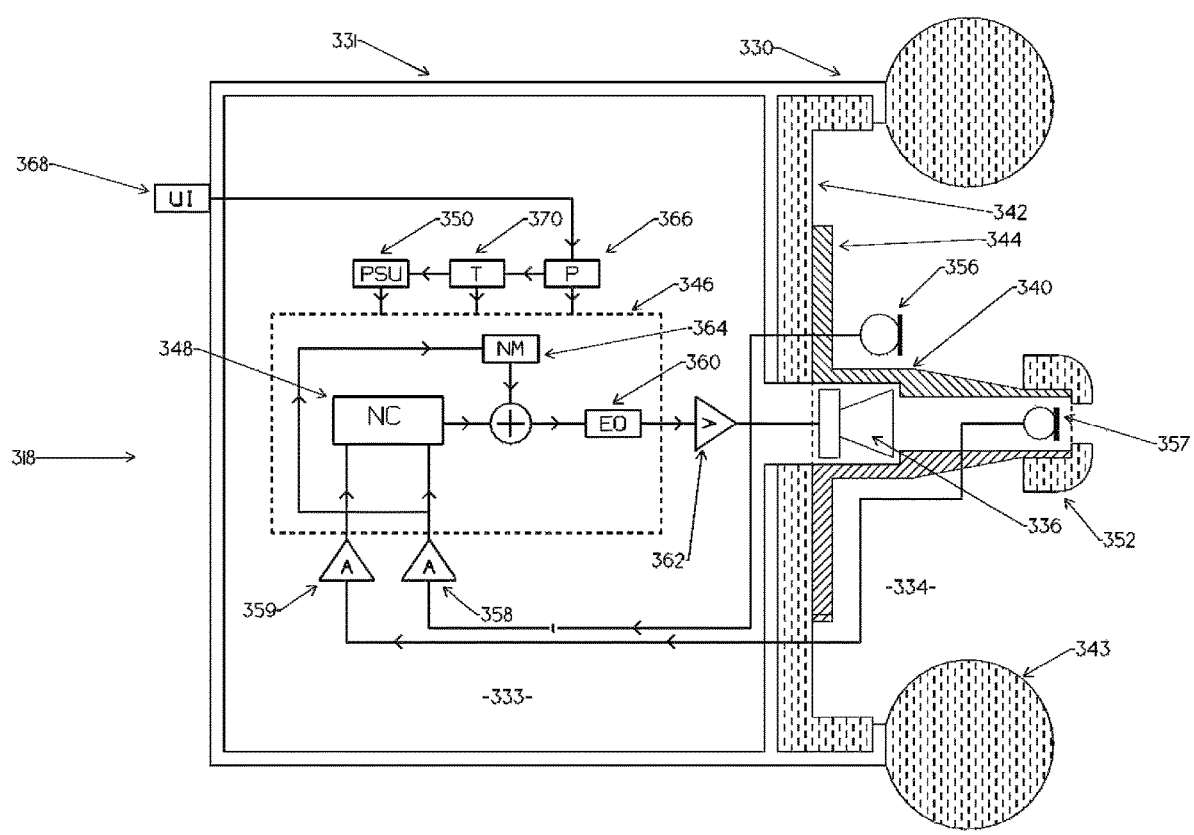

FIG. 5 shows a diagrammatic representation of a further embodiment of the electronic components of an ear covering in accordance with the invention using the feedback architecture, where there is no acoustic isolator, the speaker is in the same cavity as the audio capture device, but the audio capture device is positioned on a mount in the cavity to allow it to hear what the speaker emits, thereby creating the feedback loop and with an onboard controller; and FIG. 6 shows a diagrammatic representation of a further embodiment of the electronic components of the ear covering using the hybrid anc architecture, where the feedback audio capture device is mounted in the cavity with the speaker to hear what it emits, where the feedforward audio capture device is isolated from the speaker and positioned in the external cavity, with an external controller.

Figure 1:
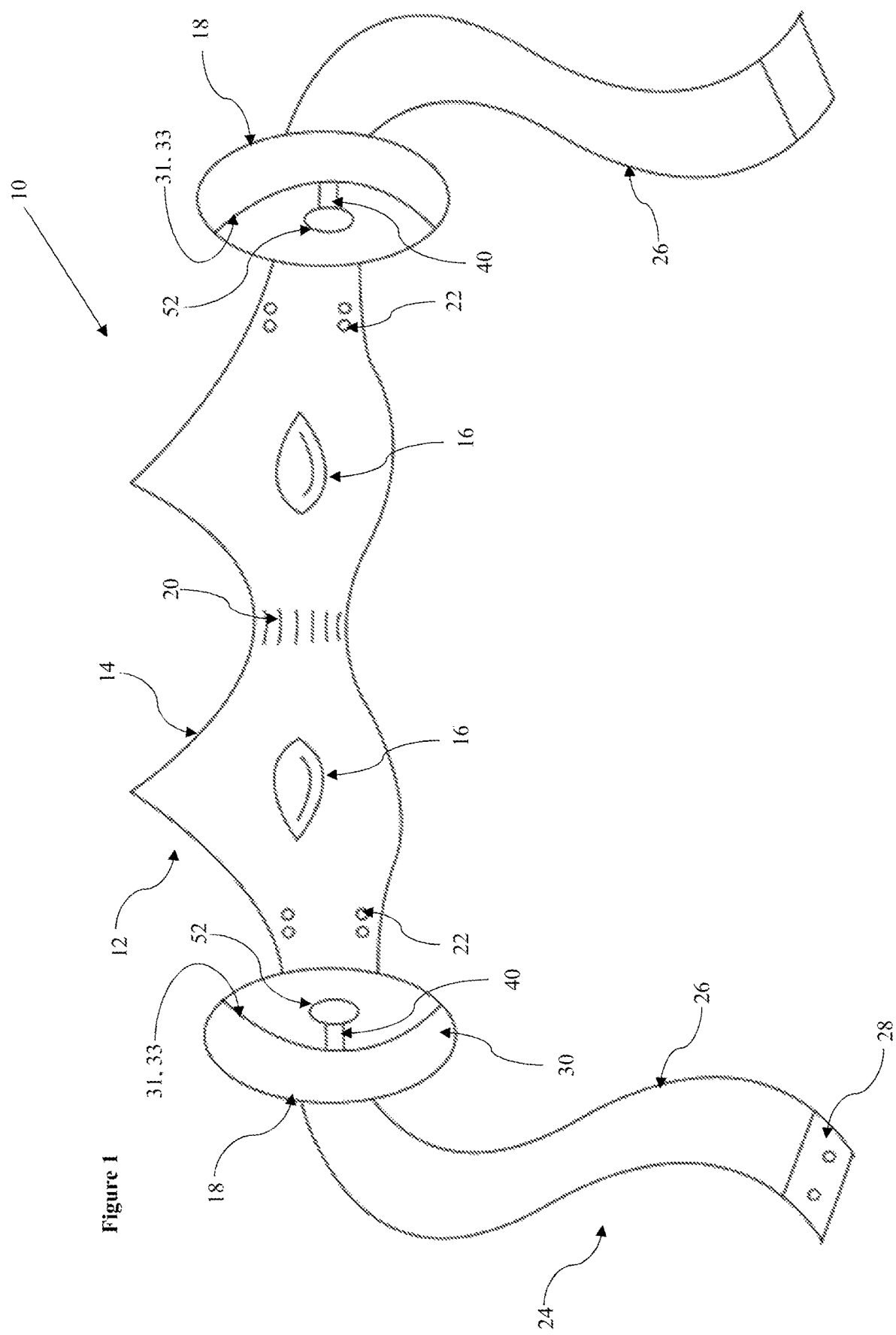
FIG. 1 shows a diagrammatic representation of a first embodiment of an ear-and-eye mask in accordance with the first aspect of the invention using feedforward or hybrid noise cancellation and an isolator stem.

Referring to FIG. 1, there is shown an ear-and-eye mask, indicated globally at 10 which is suitable for wearing by a user in order to create an effective napping environment.

The ear-and-eye mask 10 comprises a mask body 12 having an eye mask 14, preferably comprising a pair of eye coverings 16 positioned to in-use cover a user's eyes, and a pair of ear coverings 18 positioned to in-use cover a user's ears. It is preferred that the eye coverings 16 are ergonomically shaped to a user's eye sockets for comfort, but it will be equally apparent that a uniform mask portion could be provided which covers both eyes simultaneously. Each eye covering 16 can be recessed to avoid smudging make-up.

It may be possible that the eye mask 14 includes one or more indicia portions, which may be illuminable, for example, to highlight a branding of the ear-and-eye mask 10 in use.

The eye mask 14 is preferably formed from a soft material which can comfortably rest against the user's face, such as cotton, foam padding, silk, or similar material, which may be breathable for heat control, and may include one or more adjustment means for modifying a shape and/or fit of the eye mask 14 to a specific user. For example, stretchable fabric may be provided at or adjacent to a nose bridge region 20 of the eye mask 14, and/or magnetic clasps 22, preferably four magnetic clasps to permit size adjustability, may be provided to allow for adjustment of the width of the eye mask 14. The eye coverings 16 and/or nose bridge region 20 may be detachable from the sleep mask body 12 for easy cleaning.

The ear-and-eye mask 10 includes attachment means for demountably attaching to a user, and in the depicted embodiment, this is provided as a strap 24 which is engageable around the rear of a user's head. The strap 24 may preferably comprise a pair or strap portions 26 which are receivably engageable with one another, for example, via a releasable fastener 28 such as a magnetic clasp, hook and loop fastener, or popper. This allows for ready engagement of the ear-and-eye mask 10 onto a user's head. This provides room for a few centimetres adjustment, whilst the side and rear fasteners may allow for approximately six centimetres adjustability, which is suitable for covering standard head sizes for men and women. It is, however, possible that the strap 24 is fixed and that the ear cups 18 are able to move along the strap 24 to allow for a butter fit or that no strap 24 is provided, and instead the ear-and-eye mask 10 hooks over a user's ears so as to avoid tangling the user's hair or is positioned over the head.

The eye mask 14 provides a mechanism for reducing or eliminating the exposure of a user to light which can be detrimental to napping. Darkness triggers the release of melatonin, the sleep hormone which prepares the body for sleep. The ear coverings 18 are then designed to reduce or eliminate the exposure of the user to external noises, attempting to minimize disturbances for optimum napping potential.

Each ear covering 18 preferably comprises an outer cup defining a cover for the user's ear 30 when the ear-and-eye mask 10 is worn, and comprises a first passive noise-excluding member 31 which is capable of acoustically dampening noise from external sources, and may be formed from plastic materials, foam, insulators, or any appropriately acoustically absorbent material. Together they define a cavity, which contains the hollow acoustic isolator stem 40, with ergonomic tip 52, set on a planar spring 44, and the audio capture device 56.

A speaker 36 is positioned somewhere along or at the base of the hollow stem 40, which fits in to the aural cavity of the user's ear within the ear covering 18, for transmission of the noise cancelling and residual masking signals to the ear.

The audio isolator stem 40 may have an ergonomic tip 52 which will aid fit in the user's inner ear, and which may have a replaceable bud or may be easily wipeable or cleanable. This also acts as an inner acoustic seal to further prevent residual noise from entering into the ear canal and to aid in the isolation of the audio capture device from the speaker in this feedforward setup.

Figure 2:
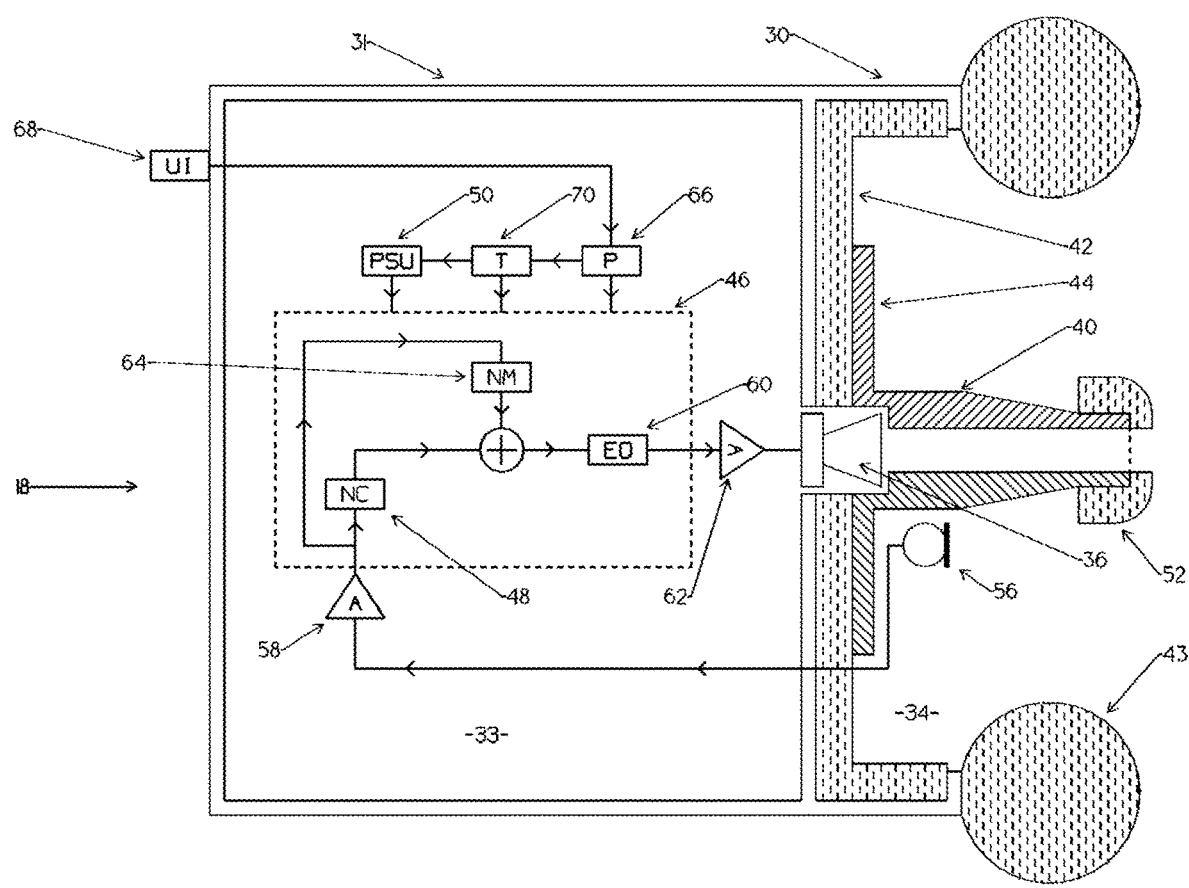
FIG. 2 shows a diagrammatic representation of the electronic components of an ear covering using the feedforward architecture and onboard control.

A more detailed representation of the ear covering 18 is shown in FIG. 2, in which a second passive noise-dampening member 42 can be seen which is positioned in the cavity 34 of the outer cup 30, plus a third passive noise dampening member 43 which is at least in contact with the rim of the outer cup to form a seal with the user's head. The passive noise-dampening members 31, 42 and 43 are preferably formed from a material which is a good absorber of noise, such as foam or padding. Such an ear covering 18, with the passive noise-dampening members 31, 42 and 43 being constructed from high-quality sound dampening materials is particularly effective at reducing higher frequencies. Member 43 may also have the advantage of being comfortable for a user's ear when the ear-and-eye mask 10 is worn. The provision of the acoustic isolator 40 also provides a locator within the ear canal, ensuring that the speaker 36 is located in the correct position for suitable noise attenuation and generation, and isolating the speaker from the audio capture device 56, also limiting the prospect of the speaker 36 falling out of the ear canal, which would otherwise be an issue for ear buds.

Preferably, there is provided a biasing element 44, such as a planar spring, which allows for adjustment of the isolator stem 40 to fit the ergonomic tip 52 into the correct location in the ear canal of the user.

The ear covering 18 includes a noise-attenuation and generation assembly 46, which may preferably, be positioned in the outer enclosure 33 as illustrated. The noise-attenuation and generation assembly 46 assists with the creation of quiet for the user.

This is achieved in this feedforward architecture by the passively attenuated signal being captured by the audio capture device 56, substantially acoustically isolated from the loudspeaker 36, which is coupled in to the user's ear canal, and feeds the signal through the amplifier 58 to the noise cancelling controller 48, which equalises and inverts the phase and sends the signal forward to the speaker 36 to cancel the residual noise in the acoustic domain, the signal generated by the noise cancelling controller is estimated and applied to the noise masking circuit which also receives the signal from the audio capture device and whose adaptive spectral analyser and generator dynamically estimates the frequency and volume of the leftover residual signal after said cancellation, and calculates and generates a compensation frequency content able to acoustically mask this residual signal following noise attenuation, which is also fed forward to the speaker 36 alongside the signal from the noise cancelling controller and renders any of the residual signal after cancellation inaudible.

The noise-cancellation controller 48 is powered by an onboard power supply 50, such as a rechargeable battery, which may allow the ear covering 18 to be used in a wireless context. Whilst the device is intended for napping purposes, it is preferred that the power supply 50 be capable of providing power for at least the duration of an extended sleep, that is, for upwards of six hours if fully charged.

In this arrangement, the noise cancelling controller 48 is preferably connected to an equalizer 60, that is, a device capable of adjusting the speaker response. The output of the noise masking circuit 64, which may in turn receive information from personalisation circuit 66, is added to the inverted signal from the noise cancelling controller, and fed forward to the equalizer 60 and then may proceed through a secondary amplifier 62, before being transmitted to the speaker 36 for transmission in to the acoustic domain.

The noise-attenuation and generation assembly 46 actively attenuates the residual signal that has passed through the passive noise-dampening members 31, 42 and 43 to reach the cavity 34. The noise cancellation controller 48 in combination with the noise masking circuit 64 using dynamic noise spectral analysis to assess the frequency and volume of the left-over residual signal following the passive noise-dampening and further cancellation, and after assessing the decibel and frequency level of this signal, uses the noise generator of the noise masking circuit digitally manufactures a suitable signal to mask it.

In addition to attenuation and adaptive masking of an input noise, it may also be possible to provide a personalisation circuit 66 which allows for user-specific modifiers to be applied to the masking noise, a select group of sounds, which provide the frequency breadth to be dynamically manipulated to mask any residual signal without losing their authenticity, might be offered to the user as an alternative to making external noises inaudible to the napping user.

There may be a dedicated user interface 68 which is positioned on the ear device or external controller which allows the user to directly affect the personalisation circuit 66 for an improved napping experience.

The user's specific hearing tendencies may be input at set-up and may stay fixed until the user wishes to change it either due to ageing or wishing to lend the product to a third party.

The isolator stem 40 used in this feedforward embodiment also serves as a locator for the speaker 36 in the ear to limit dislodgement and as a means to isolate the speaker from the audio capture device so that the audio capture device does not hear what the speaker emits. The presence of an audio isolator stem 40 with ergonomic tip 52 increases the passive attenuation for the napping user.

In use, therefore, the user is able to cover their ears with the ear coverings 18. External noises are attenuated by the passive noise-dampening members 31, 42 and 43 and the isolator stem 40 of the ear coverings 18. The attenuated noise can then be further obviated by the noise-attenuation and generation assembly 46, which reduces disturbances further.

A user may be able to set a period of noise attenuation and generation via a timer 70 of the noise-attenuation and generation assembly 46, which may be alterable via the user interface 68. A preferred default timing may be of the order of twenty minutes, for a short duration napping period which is beneficial to the user's health. However, the timer 70 can be configured to deactivate the masking noise after a predetermined or user-settable duration. The user interface 68 may comprise, for example, an activation switch, such as an on/off button, and may have activatable timer settings. Where a timer 70 is used, it may be possible to provide a dedicated wake-up sound which is a cue for the user to wake up from their nap. Similarly, an introductory or lead-in period to the attenuation created by the noise-attenuation and generation assembly 46 could be provided, allowing the user a period to sit and relax prior to their nap, the timer might also put the mask in to low power mode at the need of the timed nap to preserve battery levels.

It is also noted that several studies have noted that if light, particularly blue light, is shone into the ear canal, this can result in a measurable response in the brain, as measured via EEG. This can be used in the mitigation of the effects of jetlag. In order to enhance the post-nap rousing routine, it may therefore be viable to provide an illumination element, preferably in a wavelength range corresponding with blue light, which is aligned to illuminate the ear canal. This could for example be provided as an illumination element on the support stem 40, where provided.

Figure 3:
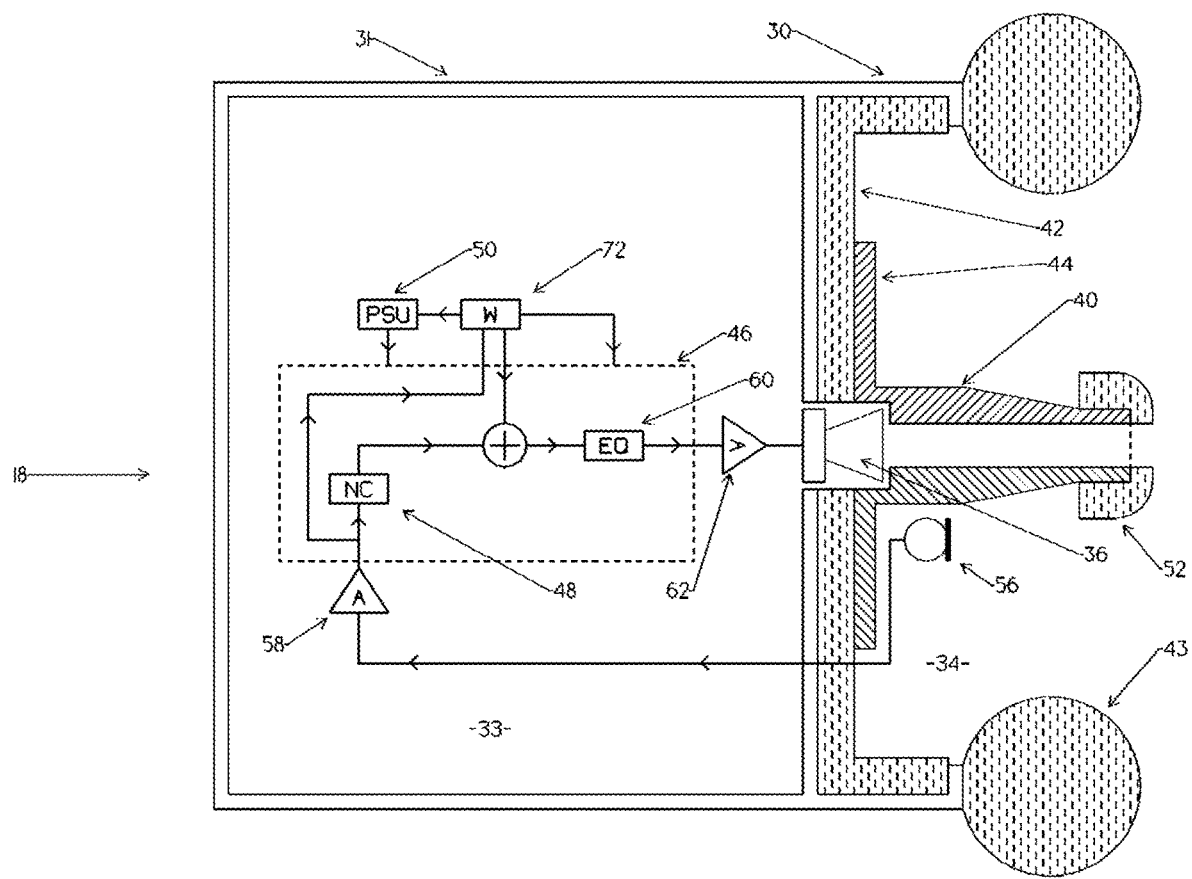
FIG. 3 shows a diagrammatic representation of the electronic components of an ear covering using the feedforward architecture, and an external controller.
Figure 3:
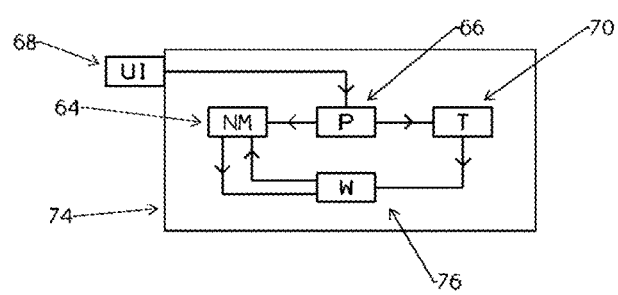

Another representation of an ear covering 18 in accordance with the first aspect of the invention is illustrated in FIG. 3, which demonstrates the above configuration but with an external controller. Identical or similar reference numerals will be used to refer to identical or similar reference numerals to those used in the above-described embodiment.

Onboard the ear-covering 18, the noise-attenuation and generation assembly 46 is fed the passively attenuated signal from the audio capture device 56 passing the signal to the amplifier 58 and the noise cancellation controller 48, which equalises and inverts the phase and sends the signal forward to the speaker 36 to cancel the ambient noise in the acoustic domain.

However, instead of an onboard noise masking circuit, which may in turn receive information from personalisation circuit 66, the audio capture device 56 is coupled via an amplifier 58 to a wireless communicator 72 which is adapted to receive and send commands to the noise masking circuit 64 via the wireless communicator 76 on an external device 74, such as a tablet computer or smartphone which optionally may have an audio capture device. The signals from the wireless controller 72 is summed with the signal from the Noise cancelling controller before being equalised and passed onward to the secondary amplifier 62, so that the resultant signal of their communications is output via the speaker 36 of the ear covering 18.

The external device 74 has a corresponding wireless communicator 76 which may be in communication with any or all of the noise attenuation and generation assembly 46, thereby allowing the user to control the functionality of the device without needing to remove it and also allowing the possibility to interact with other apps.

The control application on the external device 74 may also allow for the user to alter settings on the said device such as a do-not-disturb profile or similar which corresponds with the nap settings applied to the ear-covering 18. The control application could provide a number of other linked benefits for the user, for example, a choice of masking noises could be provided via the user interface 68, and the control application could link to a user's diary, so that nap times may be scheduled. A number of additional nap minutes or similar timing mechanism could be provided via the control application, to permit additional user control, or to provide a visual indication to third parties of a remaining nap time. Community napping aspects and mobile marketing could also be introduced.

Figure 4:
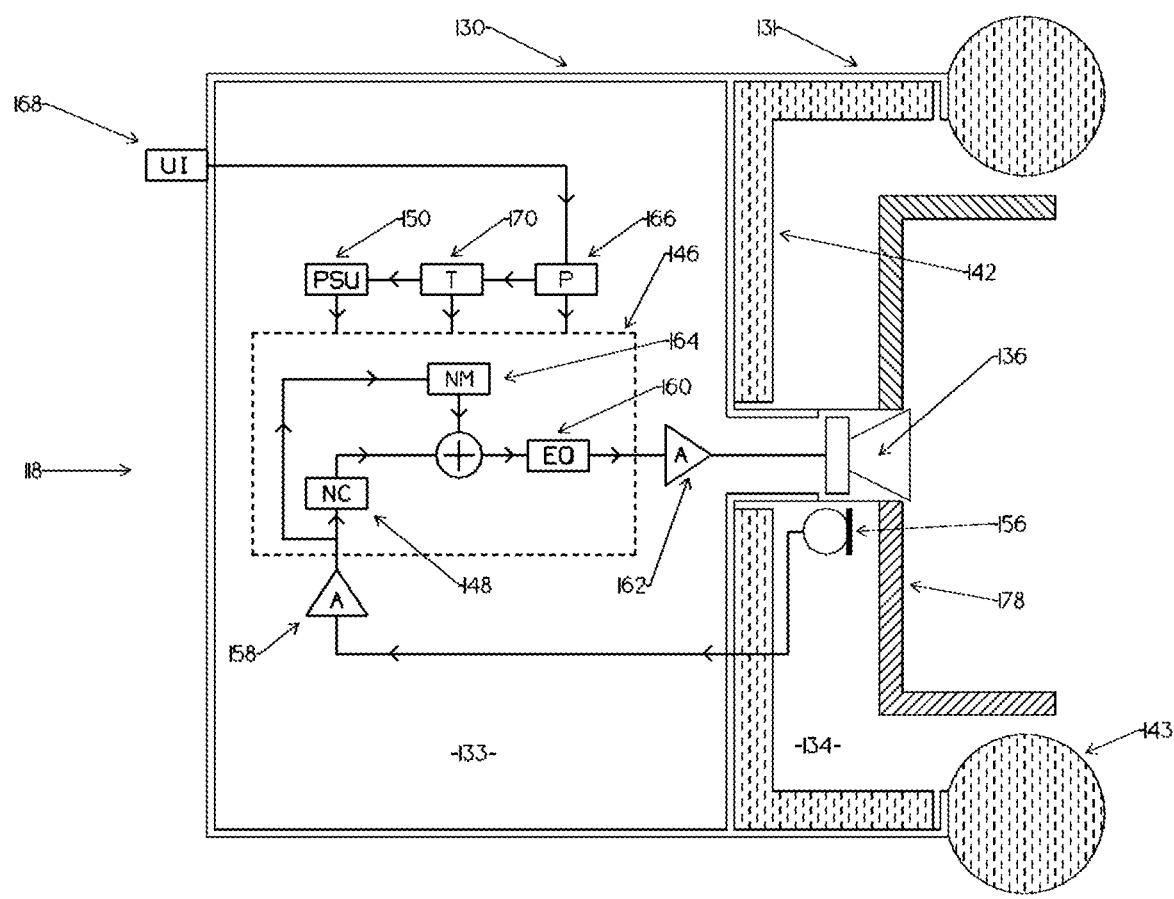
FIG. 4 shows a diagrammatic representation of a further embodiment of the electronic components of an ear covering in accordance with the first aspect of the invention using the feedforward architecture, an onboard controller, and a nested cup as the acoustic isolator.

A further alternative embodiment of the ear-covering is illustrated in FIG. 4, which operates identically to FIG. 2 only the acoustic isolator presents as an additional cup 178 in order to provide the napping user with a more traditional headphone like fit. This isolator increases the passive attenuation for the user, but in an alternate embodiment the cup could be got rid of and the audio capture device placed in the outer cavity 133.

A further alternative embodiment of the ear-covering is illustrated in FIG. 5 in which similar reference numerals are used to refer to identical or similar reference numerals to those used before.

The ear covering 218 includes a noise-attenuation and generation assembly 246, which may preferably be positioned in the enclosure 233, as illustrated. The noise-attenuation and generation assembly 246, assists with the creation of making external disturbances inaudible to the napping user. This is achieved by the passively attenuated acoustic signal from the audio capture device 256, set on the mount 240, passing through associated preamplifier 258, entering the noise controller stage 248 which generates an antiphase signal and passes it to the equaliser 260 which corrects for irregularities in the frequency response of the loudspeaker 236 and then to a power amplifier 262 which drives said loudspeaker 236 forming a negative feedback noise reduction loop.

The audio capture device simultaneously also communicates with the noise masking circuit 264, which may in turn receive information from personalisation circuit 266, to generate a masking sound which is added to the signal from the noise cancelling controller 248, passed through the equaliser 260 and then to the amplifier 262 for output by the speaker 236, to mask any residual noise left after the noise cancelling process, differential amplifier 287 prevents the masking signal increasing itself by positive feedback. Preferably the noise-attenuation and generation assembly 246 is powered by an onboard power supply 250, such as a rechargeable battery, which may allow the ear covering to be used in a wireless context. A single loudspeaker 236 may be provided coaxially at the base of the mount 240 for the audio capture device 256 venting though ports 237 or a multiplicity of loudspeakers may be provided arranged concentrically around the base of the locator 240. The audio capture device hears what the speaker emits and feeds it back to the noise attenuation and generation assembly for ongoing adjustment of the signal.

A further alternative embodiment of the ear covering is illustrated in FIG. 6 and demonstrates the hybrid, where the feedback audio capture device is mounted in the audio isolator stem with the speaker to hear what it emits, and where the feedforward audio capture device is isolated from the speaker in external cavity, with an onboard controller.

in which identical or similar reference numerals will be used to refer to identical or similar reference numerals to those used above.

The ear covering 18 includes a noise-attenuation and generation assembly 346 which may preferably be positioned in the enclosure 333 as illustrated but is split between the earcup and an external device. The passively attenuated acoustic signal passes into the electronic domain through audio capture device 356 positioned in the outside of the cup and associated preamplifier 358 then feeding into the noise controller 348 which filters and substantially inverts the phase the resultant signal is estimated and then fed to equaliser 360 which substantially corrects for irregularities in the frequency response of the loudspeaker 336 and then to a power amplifier 362 which drives said loudspeaker 336 this signal path forming a feedforward noise cancelling path. The audio capture device 356 also communicates with the noise masking circuit 364 positioned on the external controller 374 through the wireless communicators 376 372. Here the adaptive spectral analyser and generator analyse and generate a suitable masking signal to be wirelessly sent to the speaker alongside the signal from the noise cancelling controller.

A second audio capture device 357 located in front of the speaker 336 with associated preamplifier 359 hears the signal released form the speaker 336 feeds it back to the noise cancelling controller 348 and noise masking circuit to allow the latter to adjust the filtering to give the maximum noise cancellation.

It may also be possible to provide an analogue compressor as part of a noise-attenuation assembly which is capable of capping sudden interruptions of sound across the frequency spectrum. This would effectively create an analogue equivalent of the digital solution previously described.

It is therefore possible to provide an ear device, which is able to offer a slice of time controlled quiet over controlled periods of time, excluding noise and/or light from the user during this period to ensure that a restful environment can be readily created.

In general, it is therefore possible to provide an improved mechanism for creating quiet through an ear device comprising: an audio capture device 56,156,256,356,357, and a noise attenuation and generation assembly 46,146,246,346 comprising: a noise cancelling controller 48,148,248,348, and a noise masking circuit 64,164,264,364 with adaptive spectral analyser and generator, where the signal is attenuated and a suitable compensation frequency and/or volume in order to counter the input from the audio capture device 56,156,256,356,357 following attenuation created; a speaker in the cavity which emits the inverted phase from the noise cancelling controller 48,148,248,348 alongside the signal from the noise masking circuit 64, 164,264,364, which renders any of the residual signal after cancellation inaudible in the acoustic domain.

Alternatively, it could be considered that the present disclosure relates to an ear device comprising a noise-attenuation-and-generation assembly 46,146,246,346 having a digital domain, the noise-attenuation-and-adaptive generation assembly comprising, in the digital domain, a noise cancelling-circuit 48,148,248,348 and a noise masking circuit 64, 164,264,364, wherein the noise-cancelling controller 48,148,248,348 receives an input from an audio capture device 56, 156,256,356,357 and the noise masking circuit 64, 164,264,364, simultaneously receives a signal from the audio capture device whose adaptive spectral noise analyser and generator determines the frequency and/or volume after noise cancellation of the residual signal still audible to the user's ear, and generates a compensation frequency and/or volume for countering this residual signal for output by a speaker 36,136,236,336 to the user's ears.

By providing a noise masking circuit with an adaptive spectral analyser and noise generator 64,164,264,364 in addition to a noise cancelling controller 48,148,248,348 any imperfections in the noise attenuation and generation process are ameliorated further, reducing the disturbance from external noise to the user over the entire frequency range.

It may also be possible to create an analogue equivalent of the digital solution previously described.

In addition, an analogue compressor may be used as part of a noise-attenuation assembly which is capable of capping sudden interruptions of sound across the frequency spectrum.

It is therefore possible to provide an ear-and-eye mask which is able to permit napping over select periods of time, excluding noise and light from the user during this period to ensure that a restful environment can be readily created.

All of the embodiments described above can be built with either onboard control or external control where the noise attenuation and generation assembly is divided between the ear device and an external device, possibly with wireless communicators as demonstrated by FIG. 3 and FIG. 6. And the signal from the noise cancelling controller is either estimated or heard.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

The invention claimed is:

1. An ear device providing enhanced quiet for the user, the ear device comprising:
   at least one speaker respectively positioned in at least one enclosure and configured to direct sound to the user's ears;
   at least one audio capture device for capturing the sound the user's ear would hear;
   a noise-attenuation-and -generation assembly, which receives a signal from the at least one audio capture device via an amplifier and which comprises, at least one noise cancelling controller and a noise masking circuit, which comprises an adaptive spectral noise analyser and generator;
   the at least one audio capture device feed a noise-cancelling controller the sound audible to the user, the noise cancelling controller, after allowing for the passive attenuation by the ear device, generates a signal, which when fed to the at least one speaker substantially cancels this residual sound in the acoustic domain;
   simultaneously the at least one audio capture device feeds the noise masking circuit the sound still audible to the user, the adaptive spectral noise analyser and generator of the noise masking circuit analyses the frequency content of this sound, and having calculated how much the signal will be attenuated by the passive attenuation and active cancellation of the noise cancelling controller, generates a suitable frequency content to dynamically, acoustically mask this residual signal, which is summed with the signal from the noise cancelling controller and sent to the at least one speaker.

2. An ear device as claimed in claim 1, further comprising at least one outer cup which in use defines a cavity, the outer cup comprising a first passive noise-excluding member, and further passive noise-excluding and absorbing members associated with the outer cup at at least a rim of the outer cup.

3. An ear device as claimed in claim 1 which forms part of an ear-and-eye mask comprising: a mask body having an opaque eye mask positioned to in-use cover a user's eyes.

4. An ear device as claimed in claim 1, where the audio isolator to isolate the audio capture device from the speaker is: either a support stem having a protruding tip which is receivable within a user's aural cavity, or the entrance thereof, with the loudspeaker positioned at the base of this stem, or somewhere along it, the support stem being hollow so as to couple the acoustic output of the loudspeaker into the user's ear; or functions as a cup within a cup, or where the audio capture device is positioned in the outer covering of the ear device.

5. The ear device as claimed in claim 1, wherein any or all of the noise attenuation and generation assembly, are implemented by an analogue electronic circuit or a digital signal processor or a combination of the two.

6. The ear device as claimed in claim 1, wherein the noise-attenuation-and-generation assembly comprises a personalisation module, the personalisation module being adapted to receive a user input to modify the signal from the noise-attenuation-and-adaptive-generation assembly.

7. The ear device as claimed in claim 1, further comprising a timer associated with the noise-attenuation-and-generation assembly, the timer being configured to deactivate the signal from the noise-attenuation-and-generation assembly after a predetermined or user-settable duration and move the device in to low power mode.

8. The ear device as claimed in claim 1 in combination with an external computing device, which allows the noise-attenuation-and-adaptive-generation assembly to be split between the external computing device and the ear device and may also allow for the external device to enable other functions and communication with other applications.

9. The ear device as claimed in claim 1, further comprising a user interface on the ear device or on an external computer device, to permit user control of the noise-attenuation and generation assembly, and directly affect the personalisation circuit and settings and allow the user to alter settings on other external devices such as nap scheduling, nap tracking, a napping community or interaction with the user's other apps.

10. The ear device as claimed in claim 1, wherein the adaptive spectral analyser and generator of the noise masking circuit utilize algorithms to determine the frequency content of the residual signal, and generate a suitable signal, to mask this residual signal.

11. The ear device as claimed in claim 1, wherein the post passive and active cancellation signal generated by the noise cancelling controller is estimated and applied to the noise masking circuit, whose adaptive spectral noise analyser and generator dynamically analyse the frequency content of the sound from the at least one audio capture device and having calculated the leftover residual signal, dynamically generate a suitable compensation frequency content to acoustically mask it, which is sent to the speaker alongside the signal from the noise cancelling controller.

12. The ear device as claimed in claim 1, wherein there is no isolation between the audio capture device and the speaker, and the audio capture device, loudspeaker and noise cancelling controller form a feedback loop to provide ongoing attenuation at the users ear.

13. The ear device as claimed in claim 1, wherein two audio capture devices are provided; one acoustically isolated from the speaker and forming a feedforward noise cancelling path, the second in the same cavity as the speaker and feeding the residual signal after cancellation from the speaker back to the noise cancelling controller to adjust for better cancellation.

14. An ear device as claimed in claim 1, wherein since users have different hearing capabilities, often having different sensitivities to different parts of the audible spectrum, the output of the speaker is modified according to a user's personal requirements and environment, whereby after analysis determination of the residual signal, certain frequencies may be boosted or cut according to their tonal components, so that the dynamically generated masking signal is producing the most suitable masking signal for the user.

15. A method of creating enhanced napping conditions for a user, the method comprising the steps of:
providing an ear device independent or part of an ear and eye mask; and
when a napping or a quiet condition is desired putting on the ear device, whose structure reduces the impact of sound getting through to the ear, then the noise cancelling controller, having allowed for the acoustic attenuation of the passive materials, produces a signal which is the best anti-phase of the sound still getting through to the ear, and sends this to the acoustic domain, while simultaneously the frequency content of the sound getting through to the ear has been sent to the noise masking circuit where it is analysed by the adaptive spectral analyser and generator, and having allowed for the passive attenuation and active cancellation signal of the noise cancelling controller, a signal in the appropriate bandwidth is dynamically generated, which will fully mask any residual signal that might still be audible to the user at the lowest perceived masking volume, in real time, which is summed with the signal from the noise cancelling controller and sent to the speaker thereby minimizing the effect of external disturbances for the desired period of time.

\* \* \* \* \*